United States Patent [19]

Dahlin

[11] 4,169,796
[45] Oct. 2, 1979

[54] PROCESSING OF DICALCIUM PHOSPHATE AND SODIUM MONTMORILLONITE

[76] Inventor: Clarence W. Dahlin, 98 Pine St., Weston, Mass. 02193

[21] Appl. No.: 874,140

[22] Filed: Feb. 1, 1978

[51] Int. Cl.$^2$ .......................... C09K 3/00; C04B 31/20
[52] U.S. Cl. ............................................. 252/1; 34/4; 51/308; 159/DIG. 26; 424/57; 426/74
[58] Field of Search ............................... 51/308; 34/4; 159/DIG. 26; 252/1

[56] References Cited

U.S. PATENT DOCUMENTS

| | | | |
|---|---|---|---|
| 2,943,982 | 7/1960 | Dahlin | 51/308 |
| 3,348,599 | 10/1967 | Lohstoeter et al. | 159/DIG. 26 |
| 3,528,179 | 9/1970 | Smith | 159/DIG. 26 |
| 3,775,860 | 12/1973 | Barnes et al. | 159/DIG. 26 |
| 4,089,943 | 5/1978 | Roberts et al. | 51/308 |

*Primary Examiner*—Leland A. Sebastian
*Attorney, Agent, or Firm*—William Nitkin

[57] ABSTRACT

A process for forming a dispersion of dicalcium phosphate in montmorillonite clay comprising mixing sodium montmorillonite with dicalcium phosphate and some water, and subjecting the mixture to dry heat.

2 Claims, No Drawings

PROCESSING OF DICALCIUM PHOSPHATE AND SODIUM MONTMORILLONITE

BACKGROUND OF THE INVENTION

This invention relates to a method of processing dicalcium phosphate and sodium montmorillonite and more particularly to a method for the changing of sodium montmorillonite to a phosphated montmorillonite in order to produce a thoroughly dispersed stabilized calcium montmorillonite with the crystals of dicalcium phosphate becoming finely subdivided without the application of mechanical grinding action.

The present invention is concerned with hydrated dicalcium phosphate widely available commercially in substantially pure form. Dicalcium phosphate has long been known to be well suited as a polishing agent especially for relatively soft surfaces. It finds application in use as such a polishing agent for dentifrices, silver polishes, lacquer and furniture rubbing compounds and the like. It has also been widely used as a food supplement and in many preparations thereof is used in suspended form in a liquid vehicle so that fine particle size is essential to prevent settling and to maintain a stable suspension to maintain its original state of dispersion.

One problem in using dicalcium phosphate is that it is difficult to create the sufficiently fine particle size necessary for its potential uses and which fine particles hasten any process in which the dicalcium phosphate is to be consumed or utilized from a suspension thereof. Dicalcium phosphate has in some cases been provided so that it completely or substantially passes through a standard 325 mesh sieve. The maximum dimensions of the opening of such a sieve are 44×44 microns which is large compared with the desired particle size of 1-3 microns. While it might be possible to reduce the size of this material by specialized grinding methods such as micronizing or steam jet milling or the like, this is an expensive and troublesome expedient and in any case it does not appear to have been resorted to by any commercial manufacturer of dicalcium phosphate.

My U.S. Pat. No. 2,943,982, issued July 5, 1960 discloses a process for simultaneously comminuting and forming a suspension of dicalcium phosphate. In accordance with the process disclosed in that patent, there is formed a suspension of pulverized dicalcium phosphate in water which also contains suspended therein a swelling clay of the montmorillonite group. The suspension is then rapidly brought to a temperature of 200° F. or higher and maintained at such a temperature for a short time, whereupon the preparation is cooled or allowed to cool for subsequent uses.

In many cases, however, it is not desirable to use dicalcium phosphate in an aqueous suspension, and a dispersed solid phase of the substance is preferable.

SUMMARY

It is therefore an object of this invention to produce a dispersed stable solid phase of dicalcium phosphate and montmorillonite clay.

Another object of the present invention is to provide a new method for the comminution of dicalcium phosphate.

Yet another object of the present invention is to provide a method for the reduction in particle size of dicalcium phosphate by a process utilizing sodium montmorillonite clay to form a stable suspension thereof but without affecting the basic physiochemical properties of the negatively charged montmorillonite platelets.

A still further object of the present invention is to provide a suspension of finely divided dicalcium phosphate in the micron particle size range free of any tendency for crystal growth.

A further object is to produce a thoroughly dispersed stabilized calcium montmorillonite simultaneously having the dicalcium phosphate formed in small particle size being interacted and dispersed therewith a minimum of mechanical treatment.

When dicalcium phosphate is processed, as disclosed herein with a sodium montmorillonite clay, it has been found to create an extremely effective and useful shaving lotion. It also is an excellent product for polishing and cleaning dentures, and can be utilized as a highly dispersed oil soap ideal for cleansing and lubricating the body. The substance produced by the present invention can further be utilized for the liquid dispersion of various minerals, for example, calcium, magnesium, iron, manganese, etc. for medicinal purposes and can also be used to improve the stability and dispersion of lotions and ointments.

Other objects of the invention will appear as the description thereof proceeds.

DESCRIPTION OF THE PREFERRED EMBODIMENT

In accordance with the invention, there is formed a dispersion of dicalcium phosphate and sodium montmorillonite clay by first mixing the sodium montmorillonite clay with a hydrated dicalcium phosphate and some water. Thereafter the mixture is heated until it no longer contains any moisture.

The invention resulted from my experimentation with the process described in my U.S. Pat. No. 2,943,982 discussed above. In the course of my experimentation I found that the environment under which the co-suspension of dicalcium phosphate and sodium montmorillonite exists when exposed to heat need not be moist to produce results comparable to those obtained with my prior invention. Thus, contrary to the invention disclosed in that patent, the process of this invention need utilize only very little water, and also contrary to the invention disclosed in that patent, the liquid phase of the products suspended is not maintained throughout the process. Thus the mixture is subjected to heat until all moisture in the mixture has been eliminated.

I have found that as long as there is present initially water in the concentration of 2.73% by weight, the process will be operable. The heat is preferably dry heat at a temperature of 300° F. Microwave radiation can also be utilized. This temperature is generally maintained until all moisture has been eliminated.

The proportions of the ingredients are not critical. Virtually any proportions of sodium montmorillonite and dicalcium phosphate can be used. Although any ratio of these two products will permit the process to be operable, I have found that a ratio of about 2 parts sodium montmorillonite and 1.5 parts calcium phosphate is highly satisfactory. As stated above, so long as sufficient water is present to maintain an initial concentration of at least 2.73%, virtually any amount of water will permit the process to be operable, although obviously additional heat input would be necessary to eliminate extra water to the extent that more than the necessary concentration is present at the initial subjection of the mixture to heat. Preferably the water used is distilled or deionized water.

The resultant product may then be utilized in dry powder form in oils, paints, and mineral suspensions. Should it be desired to create a liquid dispersion of the solid phase obtained from the invention as thus far disclosed, the product resulting from this process can thereupon be mixed into a slurry or liquid, for example, by adding distilled demineralized water under rapid agitation. It has been noted that the solubility of the solid phase is increased and that when converted to a liquid phase, the PH is significantly lowered to the vicinity of 4.4 to 4.6. The liquid phase is additionally highly calcium saturated at about 90% with 10% sodium, and there is increased phosphorous in solution being approximately six times that of the calcium in solution.

Accordingly, while the invention has been described with particular reference to specific embodiments thereof, it will be understood that it may be embodied in a variety of forms diverse from those shown and described without departing from the spirit and scope of the invention as defined by the following claims.

I claim:

1. A process for forming a dispersion of dicalcium phosphate in sodium montmorillonite clay comprising:
   mixing two parts sodium montmorillonite clay with 1.5 parts dicalcium phosphate and not less than 2.73% distilled demineralized water by weight; and
   subjecting the mixture to dry heat in the vicinity of 300° F. until it no longer contains any water.

2. The process of comminuting and forming a liquid suspension of dicalcium phosphate comprising:
   (a) mixing two parts sodium montmorillonite clay with 1.5 parts dicalcium phosphate and not less than 2.73% distilled demineralized water by weight;
   (b) subjecting the mixture to dry heat in the vicinity of 300° F. until it no longer contains any water; and
   (c) mixing the product resulting from step b in liquid.

* * * * *